United States Patent
Wang

(10) Patent No.: US 11,024,066 B2
(45) Date of Patent: Jun. 1, 2021

(54) PRESENTATION GENERATING SYSTEM FOR MEDICAL IMAGES, TRAINING METHOD THEREOF AND PRESENTATION GENERATING METHOD

(71) Applicant: BOE TECHNOLOGY GROUP CO., LTD., Beijing (CN)

(72) Inventor: Lvwei Wang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 163 days.

(21) Appl. No.: 16/301,594

(22) PCT Filed: Feb. 28, 2018

(86) PCT No.: PCT/CN2018/077524
§ 371 (c)(1),
(2) Date: Nov. 14, 2018

(87) PCT Pub. No.: WO2018/205715
PCT Pub. Date: Nov. 15, 2018

(65) Prior Publication Data
US 2019/0122406 A1    Apr. 25, 2019

(30) Foreign Application Priority Data
May 8, 2017 (CN) .......................... 201710318888.7

(51) Int. Cl.
G06F 17/00    (2019.01)
G06T 11/60    (2006.01)
(Continued)

(52) U.S. Cl.
CPC .............. *G06T 11/60* (2013.01); *G06F 40/30* (2020.01); *G06K 9/4633* (2013.01);
(Continued)

(58) Field of Classification Search
None
See application file for complete search history.

(56) References Cited

U.S. PATENT DOCUMENTS 9,536,307 B2 * 1/2017 Kabus .................... A61B 6/469
9,968,257 B1 * 5/2018 Burt ..................... A61B 5/7267
(Continued)

FOREIGN PATENT DOCUMENTS

CN    101373518 A    9/2009
CN    101853295 A    10/2010
(Continued)

OTHER PUBLICATIONS

International Search Report and Written Opinion dated May 29, 2018 from State Intellectual Property Office of the P.R. China.
First Chinese Office Action dated Apr. 19, 2019.

*Primary Examiner* — Maikhanh Nguyen
(74) *Attorney, Agent, or Firm* — Dilworth & Barrese, LLP.; Michael J. Musella, Esq.

(57) ABSTRACT

A presentation generating system of medical images includes: a memory and a processor. The memory stores computer program instructions. The processor executes the following operations while loading the program instructions: acquiring 2D medical image; extracting image features of the medical images and transforming the image features into image feature vectors and outputting them to a first vector space established in advance; determining and outputting semantic feature vectors corresponding to the image feature vectors according to a correspondence between image feature vectors contained in the pre-established first vector space and the matching semantic feature vectors contained in the second vector space; and transforming and outputting semantic feature vectors that match the image feature vectors into corresponding natural language.

(Continued)

Further provided are a training method for the presentation generating system and a presentation generating method.

14 Claims, 3 Drawing Sheets

(51) Int. Cl.
   *G06K 9/46* (2006.01)
   *G16H 30/40* (2018.01)
   *G06N 3/08* (2006.01)
   *G16H 50/70* (2018.01)
   *G06K 9/62* (2006.01)
   *G06F 40/30* (2020.01)

(52) U.S. Cl.
   CPC ......... *G06K 9/4671* (2013.01); *G06K 9/6269* (2013.01); *G06N 3/08* (2013.01); *G16H 30/40* (2018.01); *G16H 50/70* (2018.01); *G06T 2210/41* (2013.01)

(56) References Cited

U.S. PATENT DOCUMENTS

| | | | |
|---|---|---|---|
| 10,531,807 B2* | 1/2020 | Dehghan Marvast | ........................ A61B 8/5223 |
| 10,679,345 B2* | 6/2020 | Madani | ................. G16H 30/40 |
| 2010/0235352 A1* | 9/2010 | Slutsky | ................. G06T 7/0012 707/723 |
| 2012/0027276 A1* | 2/2012 | Chono | ................. A61B 8/5223 382/128 |
| 2013/0182925 A1* | 7/2013 | Razeto | .................... G06T 7/337 382/131 |
| 2015/0302608 A1* | 10/2015 | Vilsmeier | ............... G06T 7/251 382/131 |
| 2016/0217576 A1* | 7/2016 | Kabus | .................... A61B 6/469 |
| 2018/0108124 A1* | 4/2018 | Guo | ...................... G06K 9/6274 |
| 2018/0349729 A1* | 12/2018 | Mandal | ............... G06K 9/6232 |
| 2019/0183366 A1* | 6/2019 | Dehghan Marvast | ........................ A61B 8/5223 |
| 2019/0188848 A1* | 6/2019 | Madani | ................ A61B 6/5229 |

FOREIGN PATENT DOCUMENTS

| | | |
|---|---|---|
| CN | 102053963 A | 5/2011 |
| CN | 104657350 A | 5/2015 |
| CN | 105184307 A | 12/2015 |
| CN | 105469376 A | 4/2016 |
| CN | 105654135 A | 6/2016 |
| CN | 105718952 A | 6/2016 |
| CN | 105760507 A | 7/2016 |
| CN | 105894088 A | 8/2016 |
| CN | 106021442 A | 10/2016 |
| CN | 106446526 A | 2/2017 |
| CN | 106446782 A | 2/2017 |
| CN | 107145910 A | 9/2017 |

* cited by examiner

PRESENTATION GENERATING SYSTEM FOR MEDICAL IMAGES, TRAINING METHOD THEREOF AND PRESENTATION GENERATING METHOD

TECHNICAL FIELD

Embodiments of the present disclosure relate to a presentation generating system for medical images, a training method thereof and a presentation generating method for the presentation generating system.

BACKGROUND

In order to improve diagnosis accuracy of diseases, various technologies for representing human images appear, such as nuclear magnetic resonance, computed tomography (CT), X-ray scanning and B-scan Ultrasonography, such that it is possible to obtain some key information through these technologies and thereby improving accuracy of disease diagnosis. However, as medical image data increases drastically year by year, the job of reading physicians is becoming more laborious. And since the increase amount of medical image data each year is far beyond the number increase of radiology physicians, each reading physician needs to read almost one thousand medical images every day. Overburden works lead to significantly increased probability of disease misdiagnoses.

SUMMARY

According to at least one embodiment of this disclosure, a presentation generating system of medical images is provided, which comprises: a memory storing computer program instructions and a processor, while loading the program instructions the processor executes: acquiring 2D medical images; extracting image features of the medical images and transforming the image features into image feature vectors and outputting them to a first vector space established in advance; determining and outputting semantic feature vectors corresponding to the image feature vectors according to a correspondence between image feature vectors contained in the pre-established first vector space and the matching semantic feature vectors contained in the second vector space; and transforming and outputting semantic feature vectors that match the image feature vectors into corresponding natural language.

For example, determining and outputting semantic feature vectors corresponding to the image feature vectors according to a correspondence between image feature vectors contained in the pre-established first vector space and the matching semantic feature vectors contained in the second vector space comprises: after determining pre-established image feature vectors with locations identical or similar to the image feature vectors in the first vector space, determining semantic feature vectors that have been determined as corresponding to the pre-established image feature vectors, according to the correspondence between image feature vectors contained in the pre-established first vector space and the matching semantic feature vectors contained in the second vector space, as the semantic feature vectors corresponding to the image feature vectors, and outputting the determined semantic feature vectors sequentially according to a preset output order of semantic feature vectors.

For example, transforming and outputting semantic feature vectors that match the image feature vectors into corresponding natural language comprises: transforming and outputting, by a decoder, semantic feature vectors that match the image feature vectors into corresponding natural language.

For example, the processor further execute while loading the program instructions: subjecting the acquired medical images to scaling and trimming, color enhancing and/or duplicating.

In the embodiments of this disclosure, a presentation generating method for the presentation generating system above is further provided, the method comprises: acquiring 2D medical images; extracting image features of the medical images and transforming the image features into image feature vectors and outputting them to a first vector space established in advance; determining and outputting semantic feature vectors corresponding to the image feature vectors according to the correspondence between image feature vectors contained in the pre-established first vector space and the matching semantic feature vectors contained in the second vector space; and transforming and outputting semantic feature vectors that match the image feature vectors into corresponding natural language.

In a possible embodiment of the presentation generating method in the embodiments of this disclosure, the step of determining and outputting semantic feature vectors corresponding to the image feature vectors according to the correspondence between image feature vectors contained in the pre-established first vector space and the matching semantic feature vectors contained in the second vector space comprises: after determining pre-established image feature vectors with locations identical or similar to the image feature vectors in the first vector space, determining semantic feature vectors that have been determined as corresponding to the pre-established image feature vectors according to the correspondence between image feature vectors contained in the pre-established first vector space and the matching semantic feature vectors contained in the second vector space as the semantic feature vectors corresponding to the image feature vectors and outputting the determined semantic feature vectors sequentially according to a preset output order of semantic feature vectors.

In a possible embodiment, the presentation generating method in the embodiment of this disclosure further comprises: subjecting the acquired medical images to scaling and trimming, color enhancing and/or duplicating.

According to the embodiments of this disclosure, a training method for the presentation generating system in the embodiments of this disclosure comprises: inputting a plurality of 2D medical images and a presentation document containing semantic features matching the medical images to the presentation generating system; after pre-processing the input medical images by the presentation generating system, extracting image features of the medical images, generating corresponding medical feature vectors and outputting them to a pre-established first vector space; after pre-processing the input presentation documents by the presentation generating system, extracting semantic features of the presentation documents, generating corresponding semantic feature vectors and outputting them to a pre-established second vector space; and adjusting, by the presentation generating system, mapping parameters between the image feature vectors and matching semantic feature vectors according to the image feature vectors and the matching semantic feature vectors to determine correspondence between the image feature vectors and matching semantic feature vectors.

In a possible embodiment, in the training method provided above in the embodiments of this disclosure, the pre-processing by the presentation generating system of the input medical images comprises at least one or more of scaling and trimming, by the presentation generating system, the input medical images; color enhancing, by the presentation generating system, the input medical images; and duplicating, by the presentation generating system, the input medical images.

In a possible embodiment, in the training method provided above in the embodiments of this disclosure, the pre-processing, by the presentation generating system, of the presentation documents comprises: word segmenting, by the presentation generating system, the input presentation documents.

In a possible embodiment, in the training method provided above in the embodiments of this disclosure, the step of adjusting, by the presentation generating system, mapping parameters between the image feature vectors and matching semantic feature vectors according to the image feature vectors and the matching semantic feature vectors comprises: adjusting, by the presentation generating system, mapping parameters between image feature vectors and matching semantic feature vectors, according to a loss degree between the matching semantic feature vectors and the semantic feature vectors determined with the last adjusted mapping parameters, until the loss degree between the matching semantic feature vectors and the semantic feature vectors determined with the current adjusted mapping parameters is within a preset range.

In a possible embodiment, in the training method provided above in the embodiments of this disclosure, the step of determining the loss degree between the matching semantic feature vectors and the semantic feature vectors determined with the last adjusted mapping parameters comprises: calculating the loss degree L(S, Y) between the matching semantic feature vectors S and the semantic feature vectors Y determined with the last adjusted mapping parameters according to the following formula:

$$L(S, Y) = -\frac{\sum_{t=1}^{N} \{P[RNN(S_t = Y_t) | CNN(I)]\}}{N}$$

in which, N denotes the number of sub-units contained in the recurrent neural network unit in the presentation generating system, Yt denotes the semantic feature vector determined by the t(th) sub-unit with the last adjusted mapping parameters, St denotes the t(th) semantic feature vector that the image feature vector matches, RNN(St=Yt) means that the t(th) semantic feature vector St that the image feature vector matches is the same as the semantic feature vector Yt determined by the t(th) sub-unit with the last adjusted mapping parameters, I denotes image feature vectors, and CNN(I) denotes the set of the image feature vectors.

Embodiments of the present disclosure increase reading efficiency, and at the same time improve reading quality and reduce the probability of misdiagnoses.

DETAILED DESCRIPTION

Detail description of specific implementations of a presentation generating system of medical images, a training method thereof and a presentation generating method provided in embodiments of the present disclosure will be given below with reference to accompanying drawings. It is to be noted that the described embodiments are only some of the present disclosure rather than all of them. All other embodiments obtained by one of ordinary skill in the art based on embodiments of the present disclosure without any creative work fall within the scope of the present disclosure.

It is to be noted that the presentation generating system of medical images provided in embodiments of the present disclosure are only applicable to processing of 2D (two dimension) medical images such as X-ray films rather than 3D (three dimension) medical images. Therefore, detail description will be given below mainly with respect to processing 2D medical images with the presentation generating system of medical images provided in embodiments of the present disclosure.

Figure 1:
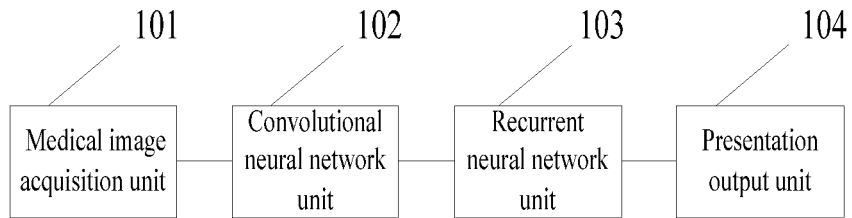
FIGS. 1, 1a and 2 are structure diagrams of the presentation generating system of medical images provided in embodiments of the present disclosure respectively.

An embodiment of the present disclosure provides a presentation generating system of medical images that may include, as shown in FIG. 1: a medical image acquisition unit 101, a convolutional neural network unit 102, a recurrent neural network unit 103 and a presentation output unit 104.

Figure 1A:
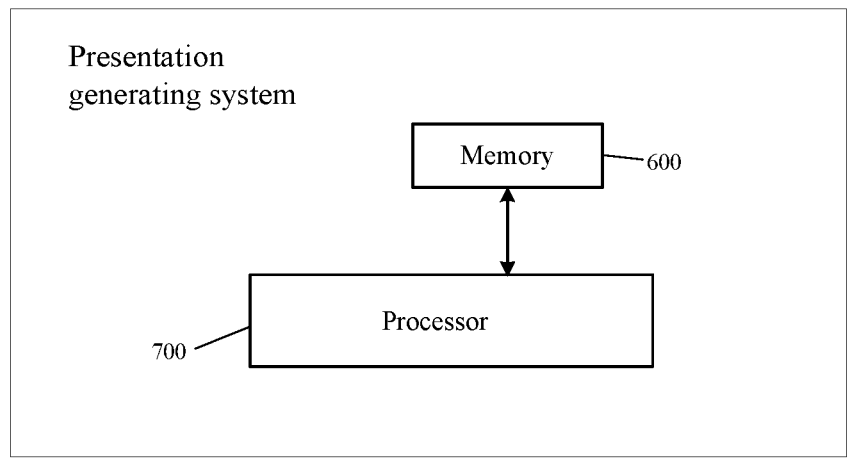

As shown in FIG. 1a, the presentation generating system of medical images may include a memory 600 and a processor 700. The memory 600 stores therein computer program instructions and while processing the above-described program instructions, the processor 700 implements functions of the medical image acquisition unit 101, the convolutional neural network unit 102, the recurrent neural network unit 103 and the presentation output unit 104. Furthermore, the medical image acquisition unit 101 may further include a pick-up head or a camera and may further include a program module implementing medical image acquisition.

The medical image acquisition unit 101 is configured to acquire 2D medical images.

The convolutional neural network unit 102 is configured to extract image features of the medical images and transform them into image feature vectors and output them to a first vector space established in advance.

The recurrent neural network unit 103 is configured to determine and output semantic feature vectors corresponding to the image feature vectors according to the correspondence between image feature vectors contained in the pre-established first vector space and the matching semantic feature vectors contained in the second vector space.

The presentation output unit 104 is configured to transform the semantic feature vectors that match image feature vectors into corresponding natural language and output the natural language.

With the above-described presentation generating system provided in embodiments of the present disclosure, based on deep learning technology and in combination with convolutional neural network technology and recurrent neural network technology, it is possible to translate 2D medical images into corresponding natural language through the presentation generating system to facilitate the doctor to further diagnose diseases, which achieves simpler and easier reading and analysis of medical images, improving reading efficiency while improving reading quality and drastically reducing the probability of mis-diagnoses.

Figure 2:
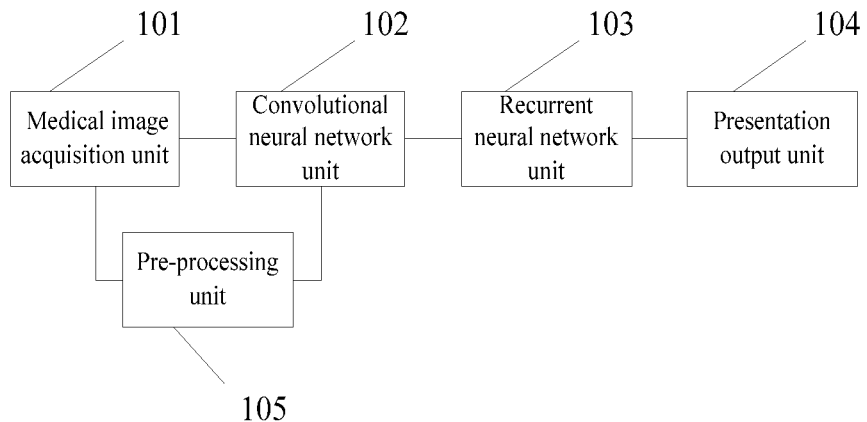

In order to allow medical images obtained by different hospital apparatuses to have uniform quality and improve identification accuracy of medical images with poor quality by the above-described presentation generating system provided in embodiments of the present disclosure, it is required to pre-process medical images to facilitate processing by the presentation generating system. Therefore, as shown in FIG. 2, the above-mentioned presentation generating system provided in the embodiment of the present disclosure may further include a pre-processing unit 105 configured to subject the acquired medical images to scaling and trimming, color enhancing and or duplicating and output them to the convolutional neural network unit 102. The function of the pre-processing unit 105 may also be implemented by the processor executing instructions stored in the memory.

According to an example of the present disclosure, the pre-processing of the acquired medical images, also known as extended processing, plays a very important role for identification performance and generalization ability. In addition, while pre-processing, it is possible to subject the acquired medical images to one or more means including scaling & trimming, coloring enhancing and duplicating. Of course it is not limited to the above-described three processing means, there may be other processing modes as long as the acquired medical images satisfy quality requirements for medical images of the presentation generating system after processing. So they are not limited herein.

Furthermore, in the above-described presentation generating system provided in embodiments of the present disclosure, the color enhancing for the acquired medical images may includes saturation processing, luminance and contrast processing of the colors. The processing is not limited to those described above as long as medical images after color enhancing satisfy quality requirements for medical images of the presentation generating system.

Further, in the above-described presentation generating system provided in embodiments of the present disclosure, subjecting the acquired medical images to duplicating is mainly because the highly imbalance of medical data which requires increasing the number of cases with special symptoms by duplication to improve accuracy of medical image reading.

Of course, when the acquired 2D medical images satisfy the image quality requirements of the presentation generating system, it is unnecessary to pre-process the acquired medical images. It is possible to input the medical images acquired by the medical image acquisition unit 101 directly to the convolutional neural network unit 102, which is not limited herein.

Generally, in a vector space, two vectors with similar meanings would be close in the vector space. Accordingly, in the pre-established first vector space, vectors corresponding to two similar image features will similarly be very close in the vector space. Therefore, according to this characteristic, it is possible to firstly find pre-established image feature vectors with locations identical or similar to the image feature vectors in the pre-established first vector space, and then determine semantic feature vectors corresponding to the image feature vectors according to the correspondence between pre-established image feature vectors and the matching semantic feature vectors contained in the second vector space. Therefore, in the above presentation generating system provided in embodiments of the present disclosure, the recurrent neural network unit 103 may be configured to, after determining pre-established image feature vectors with locations identical or similar to the image feature vectors in the pre-established first vector space, determine semantic feature vectors that have been determined as corresponding to the pre-established image feature vectors, according to the correspondence between image feature vectors contained in the pre-established first vector space and the matching semantic feature vectors contained in the second vector space, as the semantic feature vectors corresponding to the image feature vectors, and output the determined semantic feature vectors sequentially according to a preset output order of semantic feature vectors.

According to an example of the present disclosure, the correspondence between image feature vectors contained in the pre-established first vector space and the matching semantic feature vectors contained in the second vector space is determined by training and learning with large amount of data (the training process will be described in detail below) after the above-described presentation generating system provided in embodiments of the present disclosure has been established. Therefore, it is possible to guarantee that natural language information corresponding to medical images obtained by the above-described presentation generating system provided in embodiments of the present disclosure is relatively accurate and can be beneficial reference for a doctor who is diagnosing diseases.

According to an example of the present disclosure, in the above-described presentation generating system provided in embodiments of the present disclosure, while outputting sequentially the determined semantic feature vectors according to the preset output order for semantic feature vectors, said preset output order for semantic feature vectors is generally determined according to the description order commonly used by the reading physician while reading medical images. However, it is not limited thereto and may be a specific order to facilitate the doctor to better understand, which is not limited herein.

Figure 3:
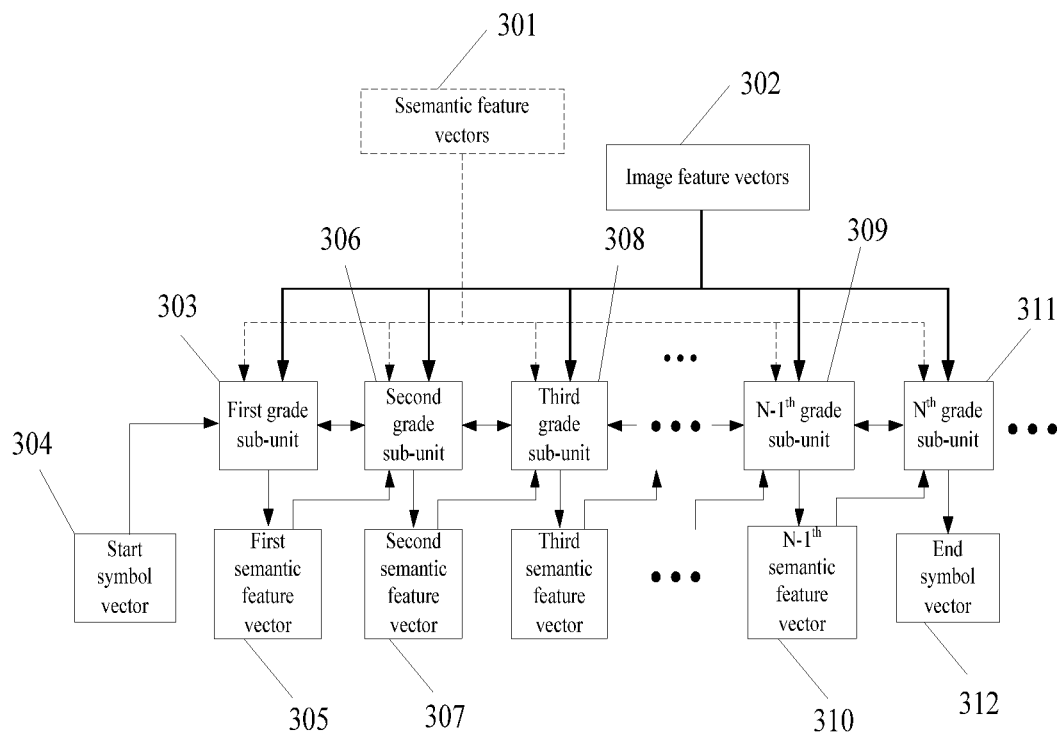
FIG. 3 is a structure diagram of a recurrent neural network unit provided in an embodiment of the present disclosure.

According to an example of the present disclosure, in the above-described presentation generating system provided in embodiments of the present disclosure, when the recurrent neural network unit 103 is configured to determine and output semantic feature vectors corresponding to the image feature vectors according to the correspondence between image feature vectors contained in the pre-established first vector space and the matching semantic feature vectors contained in the second vector space, the structure inside the recurrent neural network unit 103 may be that shown in FIG. 3. As shown in FIG. 3, the recurrent neural network unit 103 includes a plurality of cascaded sub-units. Since one sub-unit can only output one semantic feature vector, the number of sub-units is generally set according to the number of semantic feature vectors for training while training the presentation generating system. Of course, the number of sub-units may be greater than or equal to the number of semantic feature vectors for training. At the same time, each sub-unit not only inputs semantic feature vectors 301 in time sequence (dashed line shown in FIG. 3), but also inputs image feature vectors 302 (solid line shown in FIG. 3).

Further, as shown in FIG. 3, the first grade sub-unit 303 starts operation after receiving the preset start symbol vector 304, and outputs the first semantic feature vector 305 in the determined semantic feature vectors according to the correspondence between image feature vectors contained in the pre-established first vector space and the matching semantic feature vectors contained in the second vector space and the preset output order of semantic feature vectors. At the same time, the first grade sub-unit 303 not only transmits the output first semantic feature vector 305 to the second grade sub-unit 306, but also passes the processing result to the second grade sub-unit 306. The second grade sub-unit 306 outputs the determined second semantic feature vector 307 after receiving the information passed by the first grade sub-unit 303. At the same time, the second grade sub-unit 306 passes the output second semantic feature vector 307 to the third grade sub-unit 308, and passes the processing result to the third grade sub-unit 308. Similarly, until the N−1 th grade sub-unit 309 outputs the determined N−1th semantic feature vector 310 and the N−1 th grade sub-unit 309 also passes the N−1th semantic feature vector 310 and the processing result to the Nth sub-unit. Now, the Nth grade sub-unit 311 outputs a preset end symbol vector 312 that indicates the determination of semantic feature vectors is completed. Of course, except for the first grade sub-unit 303, each grade sub-unit may further passes the processing result of its grade to the upper grade sub-unit, which is not limited herein.

In the above-described presentation generating system provided in embodiments of the present disclosure, the presentation output unit 104 may be a decoder responsible for converting semantic feature vectors output by the recurrent neural network unit 103 into corresponding natural language. While one semantic feature vector may correspond to one word and may also correspond to a phrase, combining the converted natural language may obtain the analysis result of medical images, which may drastically improve reading and analysis efficiency of medical images.

Based on the same inventive concept, an embodiment of the present disclosure further provides a presentation generating method for the aforementioned presentation generating system provided in embodiments of the present disclosure. Since the principle with which the presentation generating method addresses problems is similar to that of the aforementioned presentation generating system of medical images, implementations of the aforementioned system may be referred to for implementations of the method and repeated description will not be provided any more herein.

Figure 4:
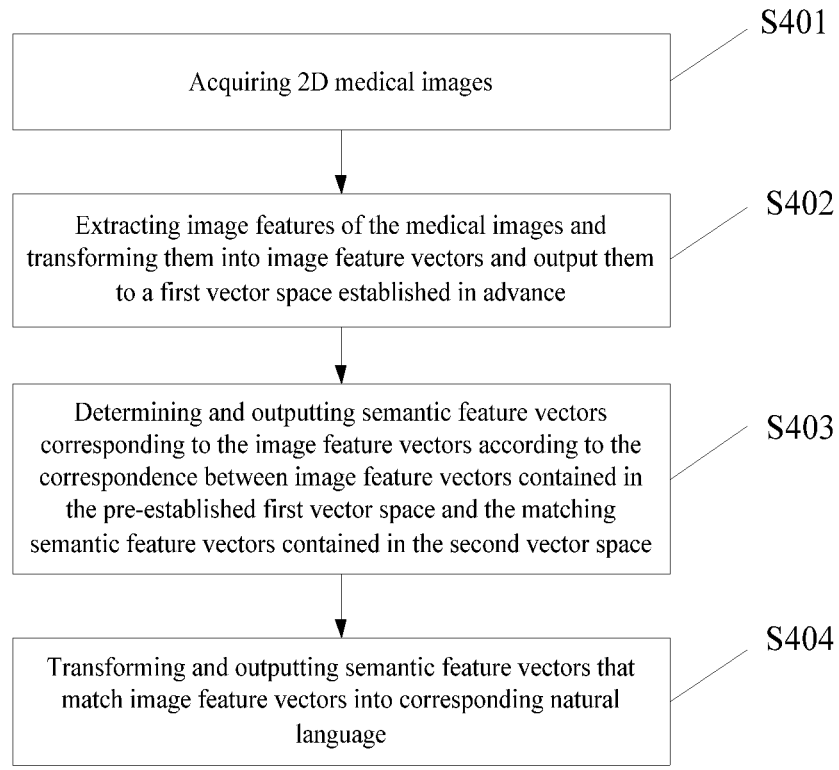
FIG. 4 is a flow chart of the presentation generating method of the presentation generating system of medical images provided in an embodiment of the present disclosure.

According to an example of the present disclosure, as shown in FIG. 4, the above-described presentation generating method provided in an embodiment of the present disclosure may include:

S401, acquiring 2D medical images;

S402, extracting image features of the medical images and transforming them into image feature vectors and output them to a first vector space established in advance;

S403, determining and outputting semantic feature vectors corresponding to the image feature vectors according to the correspondence between image feature vectors contained in the pre-established first vector space and the matching semantic feature vectors contained in the second vector space; and S404, transforming and outputting semantic feature vectors that match image feature vectors into corresponding natural language.

With the above-described presentation generating method provided in embodiments of the present disclosure, based on deep learning technology and in combination with convolutional neural network technology and recurrent neural network technology, it is possible to translate 2D medical images into corresponding natural language through the presentation generating method to facilitate the doctor to further diagnose diseases, which achieves simpler and easier reading and analysis of medical images, improving reading efficiency while improving reading quality and drastically reducing the probability of mis-diagnoses.

In order to determine and output semantic feature vectors corresponding to image feature vectors, in step S403 of the above-described presentation generating method provided in embodiments of the present disclosure, determining and outputting semantic feature vectors corresponding to the image feature vectors according to the correspondence between image feature vectors contained in the pre-established first vector space and the matching semantic feature vectors contained in the second vector space may include:

after determining pre-established image feature vectors with locations identical or similar to the image feature vectors in the pre-established first vector space, determining semantic feature vectors that have been determined as corresponding to the pre-established image feature vectors, according to the correspondence between image feature vectors contained in the pre-established first vector space and the matching semantic feature vectors contained in the second vector space, as the semantic feature vectors corresponding to the image feature vectors and outputting the determined semantic feature vectors sequentially according to a preset output order of semantic feature vectors.

The above-mentioned presentation generating method provided in the embodiment of the present disclosure may further include subjecting the acquired medical images to scaling and trimming, color enhancing and/or duplicating.

Figure 5:
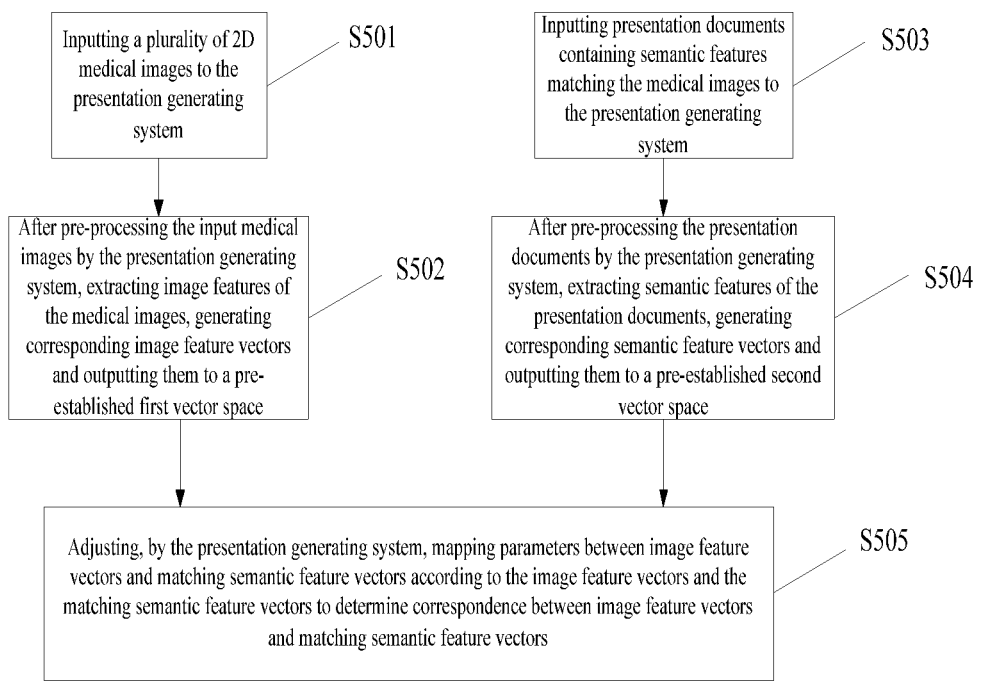
FIG. 5 is a flow chart of the training method of the presentation generating system of medical images provided in an embodiment of the present disclosure.

Based on the same inventive concept, an embodiment of the present disclosure further provides a training method for the above-described presentation generating system provided in embodiments of the present disclosure, as shown in FIG. 5, the training method may include:

S501, inputting a plurality of 2D medical images to the presentation generating system;

S502, after pre-processing the input medical images by the presentation generating system, extracting image features of the medical images, generating corresponding medical feature vectors and outputting them to a pre-established first vector space; then executing step S505;

S503, inputting presentation documents containing semantic features matching the medical images to the presentation generating system;

S504, after pre-processing the presentation documents by the presentation generating system, extracting semantic features of the presentation documents, generating corresponding semantic feature vectors and outputting them to a pre-established second vector space; and S505, adjusting, by the presentation generating system, mapping parameters between image feature vectors and matching semantic feature vectors according to the image feature vectors and the matching semantic feature vectors to determine correspondence between image feature vectors and matching semantic feature vectors.

In order to facilitate processing the acquired medical images by the presentation generating system, in step S502 of the above-described training method provided in the embodiment of the present disclosure, pre-processing, by the presentation generating system, the input medical images may include at least one or more of the following processing:

scaling and trimming, by the presentation generating system, the input medical images;

color enhancing, by the presentation generating system, the input medical images;

and duplicating, by the presentation generating system, the input medical images.

According to an example of the present disclosure, after pre-processing the input medical images, medical images are output to the convolutional neural network unit in the presentation generating system, such that the convolutional neural network unit extracts image features from the pre-processed medical images, converts the extracted image features into corresponding image feature vectors and outputs them to a pre-established first vector space to facilitate the recurrent neural network unit to determine semantic feature vectors matching the image feature vectors.

Further, it is possible to train the convolutional neural network unit with convolutional neural network (CNN) model such as the most recent CNN models, e.g., Inception-ResNet or GoogLeNet v3; and it is also possible to train the convolutional neural network unit by building CNN network according to its operation principle. Furthermore, in the training process of the convolutional neural network unit, initial parameters for the CNN network may be set to trained parameters for marked image database such as ImgeNet so that the presentation generating system may work normally.

In order to be able to acquire semantic features input to the presentation documents, it is required to pre-process the presentation documents. Therefore, in step S503 of the above-described training method provided in the embodiment of the present disclosure, pre-processing, by the presentation generating system, the input presentation documents may include:

word segmenting, by the presentation generating system, the input presentation documents.

According to an example of the present disclosure, since different doctors have different expressions and understandings for similar medical images, in order to guarantee the consistency of the finally obtained natural language, after word segmenting the presentation documents, semantic features are extracted and converted into corresponding semantic feature vectors that are output to the pre-established second vector space. In the training process of this step, it is possible to convert medical terms and the expressed semantic features into vectors by word embedding such that semantic feature vectors with similar meanings are close to each other in the second vector space.

In step S504 of the above-described training method provided in embodiments of the present disclosure, adjusting, by the presentation generating system, mapping parameters between image feature vectors and matching semantic feature vectors according to the image feature vectors and the matching semantic feature vectors may include:

adjusting, by the presentation generating system, mapping parameters between image feature vectors and matching semantic feature vectors according to the loss degree between the matching semantic feature vectors and the semantic feature vectors determined with the last adjusted mapping parameters, until the loss degree between the matching semantic feature vectors and the semantic feature vectors determined with the current adjusted mapping parameters is within a preset range.

According to an example of the present disclosure, in order to determine the loss degree between the matching semantic feature vectors and the semantic feature vectors determined with the last adjusted mapping parameters, the above-described training method provided in embodiments of the present disclosure may include:

Calculating the loss degree L(S, Y) between the matching semantic feature vectors S and the semantic feature vectors Y determined with the last adjusted mapping parameters according to the following formula:

$$L(S, Y) = -\frac{\sum_{t=1}^{N} \{P[RNN(S_t = Y_t) | CNN(I)]\}}{N}$$

in which, N denotes the number of sub-units contained in the recurrent neural network unit in the presentation generating system, Yt denotes the semantic feature vector determined by the t(th) sub-unit with the last adjusted mapping parameters, St denotes the t(th) semantic feature vector that the image feature vector matches, RNN(St=Yt) means that the t(th) semantic feature vector St that the image feature vector matches is the same as the semantic feature vector Yt determined by the t(th) sub-unit with the last adjusted mapping parameters, I denotes image feature vectors, and CNN(I) denotes the set of image feature vectors.

According to an example of the present disclosure, while calculating the loss degree L(S, Y) between matching semantic feature vectors S and semantic feature vectors Y determined with the last adjusted mapping parameters, the used formula is the loss function formula which is of course one of the loss functions. While calculating, it is not limited to using only the above-described loss function formula to calculate the loss degree L(S, Y), which is not limited herein. Further, the above-mentioned loss function may serve as an evaluation standard for the training result of the presentation generating system. The smaller the calculated loss degree L(S, Y) is, the better training the presentation generating system has received, and the more accurate the natural language obtained by processing medical images with the trained presentation generating system is.

According to an example of the present disclosure, while training the recurrent neural network unit in the presentation generating system, it is possible to use models suitable to generate natural language in recurrent neural network (RNN) models, such as Long Short-Term Memory (LSTM) and Gated Recurrent Unit (GRU) etc. Of course, it is also possible to build and improve based on the above means according to demands of the presentation generating system as long as the presentation generating system is enabled to read medical images, which is not limited herein.

Those skilled in the art should appreciate that embodiments of the present application may be provided as a method, a system or a computer program product. Therefore, the present application may be implemented in form of totally hardware embodiment, totally software embodiment or combination of software and hardware embodiments. Further, the present application may be in the form of a computer program product embodied on one or more computer usable storage media containing therein computer usable program codes (including, but not limited to disk memory and optical memory).

The present application is described with reference to flow charts and/or block diagrams of the method, device (system) and computer program product of embodiments of the present application. It should be appreciated that each step and/or block in flow charts and/or block diagrams and combinations of step and/or blocks in flow charts and/or block diagrams may be implemented by computer program instructions. It is possible to provide these computer program instructions to a general-purpose computer, a special-purpose computer, an embedded processor or a processor of other programmable data processing apparatus to generate a machine such that instructions executed by the computer or processor of other programmable data processing apparatus generate a device for implementing functions specified in one or more steps in flow charts and/or one or more blocks in block diagrams.

These computer program instructions may also be stored in computer readable memory that can guide a computer or other programmable data processing apparatus to operate in specific manner such that instructions stored in the computer readable memory generate a manufactured product including the instruction device that implements functions specified in one or more steps in flow charts and/or one or more blocks in block diagrams.

It is also possible to load these computer program instructions to a computer or other programmable data processing apparatus to execute a series of operation steps for processing implemented by the computer such that instructions executed by the computer or other programmable data processing apparatus provide steps for implementing functions specified in one or more steps in flow charts and/or one or more blocks in block diagrams.

Although preferred embodiments of the present disclosure have been described, one skilled in the art may make additional variations and modifications to these embodiments once knowing the basic innovative concepts. Therefore, the appended claims are intended to be interpreted as including preferred embodiments and all variations and modifications that fall within the scope of the present disclosure.

Embodiments of the present disclosure provide a presentation generating system of medical images of medical images, a training method thereof and a presentation generating method. The presentation generating system of medical images includes: a medical image acquisition unit, a convolutional neural network unit, a recurrent neural network unit and a presentation output unit, wherein after the medical image acquisition unit acquires 2D medical images, the convolutional neural network unit extracts image features of the medical images and converts the image features into image feature vectors that are output to a pre-established first vector space; then the recurrent neural network unit determines and outputs semantic feature vectors corresponding to image feature vectors according to the correspondence between image feature vectors contained in the pre-established first vector space and the matching semantic feature vectors contained in the second vector space; and finally, the presentation output unit converts the semantic feature vectors corresponding to the image feature vectors into corresponding natural language and outputs them to ultimately convert medical images into corresponding natural language, facilitating doctor's diagnosis of diseases. Therefore, based on deep learning technology and in combination with convolutional neural network technology and recurrent neural network technology, the presentation generating system realizes simpler and easier reading and analysis of medical images, improving reading efficiency while improving reading quality and drastically reducing the probability of mis-diagnoses.

Apparently, those skilled in the art can make modifications and variations to the present disclosure without departing from the spirit and scope of the present disclosure. Thus, if these modifications and variations of the present disclosure fall within the scope of claims and their equivalents of the present disclosure, it is intended that the present disclosure also encompass these modifications and variations.

The present application claims priority of Chinese Patent Application No. 201710318888.7 filed on May 8, 2017, the content of which is incorporated herein in its entirety by reference as a part of the present application.

What is claimed is:

1. A presentation generating system of medical images, comprising: a memory storing computer program instructions and a processor, wherein while loading the program instructions the processor executes:
   acquiring 2D medical images;
   extracting image features of the medical images and transforming the image features into image feature vectors and outputting them to a first vector space established in advance;
   matching semantic feature vectors according to the image feature vectors;
   determining and outputting the semantic feature vectors corresponding to the image feature vectors according to a correspondence between the image feature vectors contained in the pre-established first vector space and the matching semantic feature vectors contained in a second vector space; and
   transforming and outputting semantic feature vectors that match the image feature vectors into corresponding natural language,
   wherein determining and outputting semantic feature vectors corresponding to the image feature vectors according to a correspondence between image feature vectors contained in the pre-established first vector space and the matching semantic feature vectors contained in the second vector space comprises:
   after determining pre-established image feature vectors with locations identical or similar to the image feature vectors in the first vector space, determining semantic feature vectors that have been determined as corresponding to the pre-established image feature vectors, according to the correspondence between the image feature vectors contained in the pre-established first vector space and the matching semantic feature vectors contained in the second vector space, as the semantic feature vectors corresponding to the image feature vectors, and outputting the determined semantic feature vectors sequentially according to a preset output order of the semantic feature vectors.

2. The presentation generating system according to claim 1, wherein transforming and outputting semantic feature vectors that match the image feature vectors into corresponding natural language comprises:
   transforming and outputting, by a decoder, semantic feature vectors that match the image feature vectors into corresponding natural language.

3. The presentation generating system according to claim 1, wherein the processor further executes while loading the program instructions:
   subjecting the acquired medical images to scaling and trimming, color enhancing and/or duplicating.

4. A presentation generating method of medical images, comprising:
   acquiring 2D medical images;
   extracting image features of the medical images and transforming the image features into image feature vectors and outputting them to a first vector space established in advance;
   matching semantic feature vectors according to the image feature vectors;
   determining and outputting the semantic feature vectors corresponding to the image feature vectors according to a correspondence between the image feature vectors contained in the pre-established first vector space and the matching semantic feature vectors contained in a second vector space; and transforming and outputting semantic feature vectors that match the image feature vectors into corresponding natural language, wherein determining and outputting semantic feature vectors corresponding to the image feature vectors according to the correspondence between image feature vectors contained in the pre-established first vector space and the matching semantic feature vectors contained in the second vector space comprises:

after determining pre-established image feature vectors with locations identical or similar to the image feature vectors in the first vector space, determining semantic feature vectors that have been determined as corresponding to the pre-established image feature vectors according to the correspondence between the image feature vectors contained in the pre-established first vector space and the matching semantic feature vectors contained in the second vector space as the semantic feature vectors corresponding to the image feature vectors and outputting the determined semantic feature vectors sequentially according to a preset output order of the semantic feature vectors.

5. A training method for a presentation generating system of medical images, wherein the presentation generating system of medical images comprises: a memory storing computer program instructions and a processor, and while loading the program instructions the processor executes:

acquiring 2D medical images, extracting image features of the medical images and transforming the image features into image feature vectors and outputting them to a first vector space established in advance;

matching semantic feature vectors according to the image feature vectors;

determining and outputting the semantic feature vectors corresponding to the image feature vectors according to a correspondence between the image feature vectors contained in the pre-established first vector space and the matching semantic feature vectors contained in a second vector space; and transforming and outputting semantic feature vectors that match the image feature vectors into corresponding natural language;

the training method comprises:

inputting a plurality of 2D medical images and a presentation document containing semantic features matching the medical images to the presentation generating system;

after pre-processing the input medical images by the presentation generating system, extracting image features of the medical images, generating corresponding medical feature vectors and outputting them to a pre-established first vector space;

after pre-processing the input presentation documents by the presentation generating system, extracting semantic features of the presentation documents, generating corresponding semantic feature vectors and outputting them to a pre-established second vector space; and adjusting, by the presentation generating system, mapping parameters between the image feature vectors and matching semantic feature vectors according to the image feature vectors and the matching semantic feature vectors to determine correspondence between the image feature vectors and matching semantic feature vectors.

6. The training method according to claim 5, wherein the pre-processing, by the presentation generating system, of the input medical images comprises at least one or more of:

scaling and trimming, by the presentation generating system, the input medical images;

color enhancing, by the presentation generating system, the input medical images; and duplicating, by the presentation generating system, the input medical images.

7. The training method according to claim 6, wherein, pre-processing, by the presentation generating system, of the presentation documents comprises:

word segmenting, by the presentation generating system, the input presentation documents.

8. The training method according to claim 6, wherein, adjusting, by the presentation generating system, mapping parameters between the image feature vectors and matching semantic feature vectors according to the image feature vectors and the matching semantic feature vectors comprises:

adjusting, by the presentation generating system, mapping parameters between image feature vectors and matching semantic feature vectors, according to a loss degree between the matching semantic feature vectors and the semantic feature vectors determined with the last adjusted mapping parameters, until the loss degree between the matching semantic feature vectors and the semantic feature vectors determined with the current adjusted mapping parameters is within a preset range.

9. The training method according to claim 8, wherein, determining the loss degree between the matching semantic feature vectors and the semantic feature vectors determined with the last adjusted mapping parameters comprises:

calculating the loss degree L(S, Y) between the matching semantic feature vectors S and the semantic feature vectors Y determined with the last adjusted mapping parameters according to the following formula:

$$L(S, Y) = -\frac{\sum_{i=1}^{N} \{P[RNN(S_t = Y_t) \mid CNN(I)]\}}{N}$$

in which, N denotes the number of sub-units contained in the recurrent neural network unit in the presentation generating system, $Y_t$ denotes the semantic feature vector determined by the $t^{th}$ sub-unit with the last adjusted mapping parameters, $S_t$ denotes the $t^{th}$ semantic feature vector that the image feature vector matches, $RNN(S_t=Y_t)$ means that the $t^{th}$ semantic feature vector $S_t$ that the image feature vector matches is the same as the semantic feature vector Yt determined by the $t^{th}$ sub-unit with the last adjusted mapping parameters, I denotes image feature vectors, and CNN(I) denotes the set of the image feature vectors.

10. The training method according to claim 5, wherein the pre-processing, by the presentation generating system, of the presentation documents comprises:

word segmenting, by the presentation generating system, the input presentation documents.

11. The training method according to claim 10, wherein, adjusting, by the presentation generating system, mapping parameters between the image feature vectors and matching semantic feature vectors according to the image feature vectors and the matching semantic feature vectors comprises:
adjusting, by the presentation generating system, mapping parameters between image feature vectors and matching semantic feature vectors, according to a loss degree between the matching semantic feature vectors and the semantic feature vectors determined with the last adjusted mapping parameters, until the loss degree between the matching semantic feature vectors and the semantic feature vectors determined with the current adjusted mapping parameters is within a preset range.

12. The training method according to claim 11, wherein, determining the loss degree between the matching semantic feature vectors and the semantic feature vectors determined with the last adjusted mapping parameters comprises:
calculating the loss degree L(S, Y) between the matching semantic feature vectors S and the semantic feature vectors Y determined with the last adjusted mapping parameters according to the following formula:

$$L(S, Y) = -\frac{\sum_{t=1}^{N}\{P[RNN(S_t = Y_t) | CNN(I)]\}}{N}$$

in which, N denotes the number of sub-units contained in the recurrent neural network unit in the presentation generating system, $Y_t$ denotes the semantic feature vector determined by the $t^{th}$ sub-unit with the last adjusted mapping parameters, $S_t$ denotes the $t^{th}$ semantic feature vector that the image feature vector matches, $RNN(S_t=Y_t)$ means that the $t^{th}$ semantic feature vector $S_t$ that the image feature vector matches is the same as the semantic feature vector Yt determined by the $t^{th}$ sub-unit with the last adjusted mapping parameters, I denotes image feature vectors, and CNN(I) denotes the set of the image feature vectors.

13. The training method according to claim 5, wherein adjusting, by the presentation generating system, mapping parameters between the image feature vectors and matching semantic feature vectors according to the image feature vectors and the matching semantic feature vectors comprises:
adjusting, by the presentation generating system, mapping parameters between image feature vectors and matching semantic feature vectors, according to a loss degree between the matching semantic feature vectors and the semantic feature vectors determined with the last adjusted mapping parameters, until the loss degree between the matching semantic feature vectors and the semantic feature vectors determined with the current adjusted mapping parameters is within a preset range.

14. The training method according to claim 13, wherein determining the loss degree between the matching semantic feature vectors and the semantic feature vectors determined with the last adjusted mapping parameters comprises:
calculating the loss degree L(S, Y) between the matching semantic feature vectors S and the semantic feature vectors Y determined with the last adjusted mapping parameters according to the following formula:

$$L(S, Y) = -\frac{\sum_{t=1}^{N}\{P[RNN(S_t = Y_t) | CNN(I)]\}}{N}$$

in which, N denotes the number of sub-units contained in the recurrent neural network unit in the presentation generating system, $Y_t$ denotes the semantic feature vector determined by the t(th) sub-unit with the last adjusted mapping parameters, $S_t$ denotes the t(th) semantic feature vector that the image feature vector matches, $RNN(S_t=Y_t)$ means that the t(th) semantic feature vector $S_t$ that the image feature vector matches is the same as the semantic feature vector Yt determined by the t(th) sub-unit with the last adjusted mapping parameters, I denotes image feature vectors, and CNN(I) denotes the set of the image feature vectors.

* * * * *